United States Patent
Galbraith et al.

(10) Patent No.: US 10,099,258 B2
(45) Date of Patent: Oct. 16, 2018

(54) ARTICLE CONVEYING SYSTEM WITH DIFFUSE ILLUMINATION

(71) Applicant: Compac Technologies Limited, Hamilton (NZ)

(72) Inventors: Duncan Galbraith, Hamilton (NZ); Michael Edmondson, Hamilton (NZ); Simon Knightley, Hamilton (NZ)

(73) Assignee: Compac Technologies Limited, Hamilton (NZ)

( * ) Notice: Subject to any disclaimer, the term of this patent is extended or adjusted under 35 U.S.C. 154(b) by 0 days.

(21) Appl. No.: 15/564,140

(22) PCT Filed: Apr. 8, 2016

(86) PCT No.: PCT/NZ2016/050058
§ 371 (c)(1),
(2) Date: Oct. 3, 2017

(87) PCT Pub. No.: WO2016/163896
PCT Pub. Date: Oct. 13, 2016

(65) Prior Publication Data
US 2018/0078972 A1    Mar. 22, 2018

(30) Foreign Application Priority Data

Apr. 9, 2015 (NZ) .................................. 706771
Feb. 17, 2016 (NZ) .................................. 717040

(51) Int. Cl.
*B07C 5/00* (2006.01)
*B07C 5/342* (2006.01)
(Continued)

(52) U.S. Cl.
CPC ............ *B07C 5/3422* (2013.01); *B07C 5/342* (2013.01); *G01N 21/8806* (2013.01);
(Continued)

(58) Field of Classification Search
CPC .................................................... B07C 5/3422
(Continued)

(56) References Cited

U.S. PATENT DOCUMENTS 3,235,739 A * 2/1966 Rottmann .......... G01N 21/9036
209/526
3,939,063 A * 2/1976 Epperson .............. B07C 5/3404
209/3.1
(Continued)

FOREIGN PATENT DOCUMENTS

GB          2165942 A  *  4/1986  ........... B07C 5/3408
GB          2165942 A      4/1986
WO      WO-0179092 A1 * 10/2001  ........... B07C 5/3422

*Primary Examiner* — Terrell H Matthews
(74) *Attorney, Agent, or Firm* — Gable Gotwals

(57) ABSTRACT

This invention relates to an article inspection system having one or more endless article conveyors configured to convey articles along one or more conveying paths. One or more light sources and one or more light diffusers are provided, wherein each light diffuser is positioned substantially at or below the level of the articles when conveyed along the conveying paths so as to illuminate, using light from the one or more light sources, at least side portions of the articles with substantially diffuse light when the articles are conveyed along the conveying path(s). At least one camera is positioned to image articles which are conveyed along the conveying paths.

17 Claims, 7 Drawing Sheets

(51) Int. Cl.
  *G03B 15/06* (2006.01)
  *G01N 21/88* (2006.01)
  *G01N 21/89* (2006.01)
(52) U.S. Cl.
  CPC ......... *G01N 21/8901* (2013.01); *G03B 15/06* (2013.01); *B07C 2501/009* (2013.01); *G01N 2021/8819* (2013.01)
(58) Field of Classification Search
  USPC .................................................. 209/552, 938
  See application file for complete search history.

(56) References Cited

U.S. PATENT DOCUMENTS

| | | | | |
|---|---|---|---|---|
| 4,483,615 A * | 11/1984 | Bieringer | ............ | G01N 21/896 209/526 |
| 4,776,466 A * | 10/1988 | Yoshida | ................ | B07C 5/3408 209/565 |
| 5,000,569 A * | 3/1991 | Nylund | ................... | A21C 15/00 250/226 |
| 5,520,290 A * | 5/1996 | Kumar | ..................... | B07C 5/3422 198/349.1 |
| 5,636,024 A * | 6/1997 | Crookham | ........... | G01M 11/005 356/237.1 |
| 5,981,892 A * | 11/1999 | Baird | ........................ | B07C 5/34 209/590 |
| 6,060,677 A * | 5/2000 | Ulrichsen | ............... | B07C 5/342 209/577 |
| 6,199,679 B1 * | 3/2001 | Heuft | .................... | B07C 5/3408 198/346.2 |
| 6,373,520 B1 * | 4/2002 | Cadieux, Jr. | .......... | B07C 5/3422 348/125 |
| 6,693,274 B2 * | 2/2004 | Baird | ........................ | B07C 5/06 156/360 |
| 8,397,905 B1 * | 3/2013 | Tritz | .................... | B65G 15/105 198/817 |
| 2006/0037892 A1 * | 2/2006 | Blanc | ................. | G01N 21/8806 209/577 |

* cited by examiner

ARTICLE CONVEYING SYSTEM WITH DIFFUSE ILLUMINATION

CROSS-REFERENCE TO RELATED APPLICATIONS

This United States application is the National Phase of PCT Application No. PCT/NZ2016/050058 filed 8 Apr. 2016, which claims priority to New Zealand Patent Application No. 706771 filed 9 Apr. 2015 and to Patent Application No. 717040 filed 17 Feb. 2016, each of which is incorporated herein by reference.

BACKGROUND OF THE INVENTION

Field of Invention

The invention generally relates to the field of article conveying systems, article inspection systems and article sorting systems. More particularly, the invention relates to such systems with diffuse illumination and irradiation sources.

Background to the Invention

Conveyors are often used in grading machines to transport articles through various measurement stages and to discharge the articles to sort them dependent on the measurements.

A common type of object that is graded and sorted by such a conveyor system is fruit. Fruit may be sorted based on criteria such as weight, shape, colour, ripeness and any other characteristic. Conveyor systems comprise devices to measure these characteristics while the fruit is being transported. For example, the characteristics can be detected and measured by visual scanning devices positioned above the conveyor. The position of each fruit and its respective characteristics can be tracked so that a discharge mechanism causes items of fruit to be unloaded from the conveyor and sent to the required destination, for example towards a chute or onto another conveyor.

Similar systems can be used to grade and sort other types of product based on similar characteristics or other characteristics specific to the type of product.

To ensure clear images of the articles are captured, the articles are usually illuminated or (in the case of non-visible light) irradiated. It is generally desirable for articles to be illuminated evenly. Uneven illumination or other illumination problems may impact on the quality of images and the ability to analyse them. In turn, this may lead to errors in product sorting, which are not desired.

Conventionally two types of light source are used to illuminate items in an automatic fruit sorting system: 1) polarised direct illumination; and 2) diffused illumination.

Polarised direct illumination relies upon light sources pointed at the articles to be sorted and cross-polarising the illumination source and image capture equipment. Cross-polarisation removes the specular (i.e. direct or mirror-like) reflection of light from the fruit as seen by the image capture equipment and leaves only the diffused reflections of interest in the image. Polarised direct illumination has several disadvantages. Firstly, polarising material can be costly, particularly high wavelength polarisers. Secondly, it can be difficult (or expensive) to handle a wide range of illumination wavelengths using polarisers. Different types of polariser may be required for ultra violet, visible and infra-red parts of the spectrum and it is common for each of these polarisers to interfere adversely with light in other parts of the spectrum. Thirdly, direct illumination systems typically have a limited number of discrete light sources that tend to produce shadows across article inspection scenes. In the case of fruit inspection this is particularly disadvantageous since the geometric shape of fruit varies, and this introduces image artefacts that are difficult to attribute as shadows. Fourthly, polarisers cut out a high proportion of the incident light, which reduces the quality of the resulting images and consequently the information that can be gained from the images.

Diffused illumination environments can offer advantages over polarised direct illumination, however they can be particularly sensitive to geometric variations of inspected articles and therefore pose challenges in maintaining a consistent behaviour within production environments. In some cases, diffused illumination can avoid the need for polarisers, thereby alleviating the cost and multispectral constraints of polarisers and producing an even specular reflection across the surface of the inspected articles, e.g. fruit. One disadvantage of not using cross-polarisation between light source and image capture equipment is that any deviation from an ideal geometric layout tends to produce specular reflection that may hide the useful diffused reflection on a portion of the surface of the articles. For fruit grading systems, the inspected objects themselves have considerable geometric variation and are conveyed through an inspection area. This means the geometric conditions during inspection are practically never ideal and image artefacts (e.g. dark spots, colourshift, bright reflections, shadows, speckles or the like) are often present that are difficult for machines to accurately interpret or there may be regions of a fruit's surface that are not inspected.

Further complicating the use of diffused illumination environments for fruit inspection is the common use of multiple cameras and the linear translation of the fruit throughout the inspection site. This creates a problem due to the variance of Fresnel reflections for a change in angle of incidence. The variance in Fresnel reflections has the practical manifestation that an illumination configuration suited for one camera view may have negative effects for other camera views. The same drawback also applies to the translation of the fruit: an illumination configuration appropriate for one location along the conveyor may not be adequate for inspecting the same fruit in another location.

Diffused illumination environments therefore have difficulties in achieving satisfactory results where there is large variability in inspected articles. To cope with such variability, the negative effects that can be caused by diffused illumination are reduced by configurations that tend not to offer ideal imaging conditions.

The MAF tunnel cabinet MAF Globalscan 5, Unitec Cherry Vision cabinet and Apple Retrofit are examples of the application of diffused illumination environments to fruit inspection. Another example is disclosed in US Patent Publication No. 2006/0037892. These machines use a source of diffuse illumination positioned above the fruit that, while relatively robust to the negative effects of image artefacts, suffer from poor radial uniformity on a fruit's surface and with automated inspection often perform worse than polarised direct illumination environments. Such machines have therefore tended to not compete with polarised direct illumination systems in terms of performance, but have offered a lower cost version due to the lower manufacturing costs.

OBJECT OF THE INVENTION

It is an object of the invention to provide an improved article inspection system, article conveying system and/or article sorting system. Alternatively, it is an object to provide an improved article illumination device for use in such systems. Alternatively, it is an object of the invention to at least provide the public with a useful choice.

SUMMARY OF THE INVENTION

According to a first aspect of the invention, there is provided an article inspection system comprising:
one or more endless article conveyors configured to convey articles along one or more conveying paths;
one or more light sources and one or more light diffusers, wherein each light diffuser is positioned substantially at or below the level of the articles when conveyed along the conveying paths so as to illuminate, using light from the one or more light sources, at least side portions of the articles with substantially diffuse light when the articles are conveyed along the conveying path(s); and
at least one camera positioned to image articles conveyed along the conveying paths.

It will be understood that the terms "illuminate", "illumination" and the like are used throughout this document to refer to the act of exposing something to any kind of light, including visible and non-visible light (e.g. infra-red or ultra violet light). For the purposes of this document, said terms should be considered synonymous with the terms "irradiate", "irradiation" and the like, unless the context clearly requires otherwise.

Preferably, each light diffuser comprises a light emitting surface adjacent at least one of the conveying paths and elongate in substantially the same orientation as the conveying paths.

More preferably, the light emitting surface has a length so that parts of the light emitting surface are substantially adjacent a plurality of articles when conveyed along a conveying path.

In preferred embodiments, the inspection system comprises one or more lane dividers, each lane divider being positioned adjacent one of the conveying paths and being elongate substantially along the respective adjacent conveying paths. In the case that the inspection system comprises a plurality of conveying paths, at least one of lane dividers is positioned between two of the conveying paths. More preferably, each lane divider comprises:
one or more walls substantially facing the respective adjacent conveying paths; and
at least one of the light diffusers for diffusing light with which the respective adjacent conveying paths are illuminated.

Preferably, the walls of the lane dividers are angled upwards.

More preferably, the light diffusers comprise a plurality of first translucent light diffusers and at least a portion of each wall of the lane divider is formed from one of the first translucent light diffusers.

More preferably, each lane divider further comprises at least one of the light sources for illuminating the articles.

Preferably, each lane divider comprises an elongate lane divider housing comprising the lane divider walls. More preferably, the lane divider housing has a cross-sectional shape in the form of an arch, bell-shape, upturned U or upturned V.

More preferably, the light diffusers comprise a plurality of reflective light diffusers and each lane divider comprises one or more of the reflective light diffusers configured to diffuse and reflect light received from one of the light sources such that the diffuse and reflected light is incident on the respective first translucent light diffuser(s).

Preferably, the light diffusers comprise a plurality of second translucent light diffusers and each lane divider comprises one or more of the second translucent light diffusers positioned to diffuse light emitted by the plurality of light sources so that diffuse light is incident on the reflective light diffuser(s).

In preferred embodiments, each lane divider comprises a plurality of light sources housed by the elongate line divider housing, the plurality of light sources being spaced along the length of the lane divider.

In preferred embodiments, the inspection system comprises one or more upper light sources configured, in combination with one or more of the light diffusers, to illuminate at least upper portions of the articles with substantially diffuse light when the articles are conveyed along the conveying path(s).

Preferably, the inspection system comprises a cover member configured to substantially cover the one or more conveying paths along at least the part of the length of the conveying paths illuminated by the one or more light sources and to substantially inhibit or prevent light from light sources other than the one or more light sources and the one or more upper light sources from illuminating the articles.

More preferably, the cover member is comprised of a light diffusing bottom surface configured to diffuse light from the one or more upper light sources so that diffuse light illuminates the upper portions of the articles.

More preferably, the upper light sources are configured to project light upwards onto the light diffusing bottom surface of the cover member.

In preferred embodiments of the invention, the one or more light sources and the one or more upper light sources are configured to illuminate the articles with substantially equal light intensity. More preferably, the inspection system comprises a light intensity controller configured to control the intensity of the one or more light sources and the one or more upper light sources.

Preferably, the inspection system comprises a plurality of cameras and an image controller for selectively controlling each of the plurality of cameras to image the articles conveyed along the conveying paths and for selectively controlling illumination of the one or more light sources and the one or more upper light sources, the selective control of imaging by the cameras being dependent on the selective control of illumination by the one or more light sources and the one or more upper light sources.

Preferably, the conveyors are configured to convey the articles along a plurality of conveying paths and one or more of the light diffusers are positioned between conveying paths.

According to a second aspect of the invention, there is provided an article conveyor system comprising:
one or more endless article conveyors configured to convey articles along one or more conveying paths; and
one or more elongate diffuse light sources positioned to illuminate the articles when conveyed along the conveying path(s), each of the elongate diffuse light sources being positioned adjacent one of the conveying paths.

Preferably, the conveyors are configured to convey the articles along a plurality of conveying paths and one of the elongate diffuse light sources is positioned between each pair of adjacent conveying paths.

More preferably, the elongate diffuse light sources are positioned substantially at or below the level of the articles so as to illuminate at least side portions of the articles when the articles are conveyed along the conveying paths.

According to a third aspect of the invention, there is provided an article inspection system comprising:

the article conveyor system of the second aspect of the invention; and at least one camera positioned to image articles conveyed along the conveying paths.

According to a fourth aspect of the invention there is provided an article sorting system comprising:

the article inspection system of the first and/or third aspects of the invention; and discharge means for selectively discharging articles from the article conveyors to one or more discharge locations.

Preferably, the sorting system comprises means for controlling the discharge means based on analysis of images captured by the at least one camera.

Preferably, the sorting system comprises means for generating data indicative of how the articles should be sorted dependent on the analysis of the images.

More preferably, the sorting system comprises analysis means for receiving image data based on the images and analysing the image data to determine characteristics of the imaged articles.

According to a fifth aspect of the invention, there is provided an article illumination device for a conveying system comprising:

one or more diffuse light sources;

a body accommodating the one or more diffuse light sources, wherein the article illumination device is configured, in use, to be positioned adjacent a conveying path of the conveying system so that the diffuse light source(s) illuminate articles when conveyed along the conveying path, wherein the body is elongate in substantially the same orientation as the conveying path and has a length such that respective parts of a light emitting surface of the illumination device are substantially adjacent each of a plurality of articles when conveyed along the conveying path.

Preferably, the one or more diffuse light sources comprises a plurality of light sources housed in the body.

Preferably, the article illumination device comprises a wall diffuser forming at least a part of a wall of the body, the wall substantially facing the conveying path. Preferably, the wall is angled upwards.

Preferably, the body has a cross-sectional shape in the form of an arch, upturned U or upturned V.

More preferably, the one or more diffuse light sources comprises at least one reflective light diffuser configured to diffuse and reflect light received from each of the light sources such that the diffuse and reflected light is incident on the wall diffuser.

Preferably, the one or more diffuse light sources comprises a plurality of source light diffusers positioned to diffuse light emitted by the plurality of light sources so that diffuse light is incident on the reflective light diffuser(s).

In preferred embodiments, the light sources are spaced along the length of the body.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

It has been identified that some prior art sorting systems that illuminate articles using diffuse lighting sources perform poorly because of inadequate illumination around the sides of articles. Embodiments of the invention therefore provide conveyor systems in which diffuse lighting is used to illuminate the sides and, in particular, the lower sides of articles to be sorted.

In general terms, embodiments of the invention provide one or more diffuse light sources alongside the lanes of conveying systems to provide diffuse lighting against the sides of conveyed articles. The diffuse light sources are elongate, and typically extend along the length of a conveyer cabinet where articles are imaged or otherwise inspected. Diffuse lighting may be provided in dividers between the lanes so that each lane of conveyed articles has a diffuse lighting source immediately adjacent the conveyer on either side. This arrangement has been found to provide an improved lighting environment in a conveyer cabinet, resulting in improved image quality and therefore improved article sorting.

Throughout this specification it will be understood that the term "diffuse light source" refers to any source of diffuse light. To provide diffuse light, a light source (i.e. a device that produces light) may illuminate an article directly or indirectly. A diffuser that diffuses light produced by a non-diffuse light source may be considered a diffuse light source. Alternatively, the diffuser and light source together may be considered a diffuse light source. That is, the source of light and the means of diffusing the light from the source may be embodied in the same device or different devices.

Introduction to Conveying/Sorting System

Figure 1:
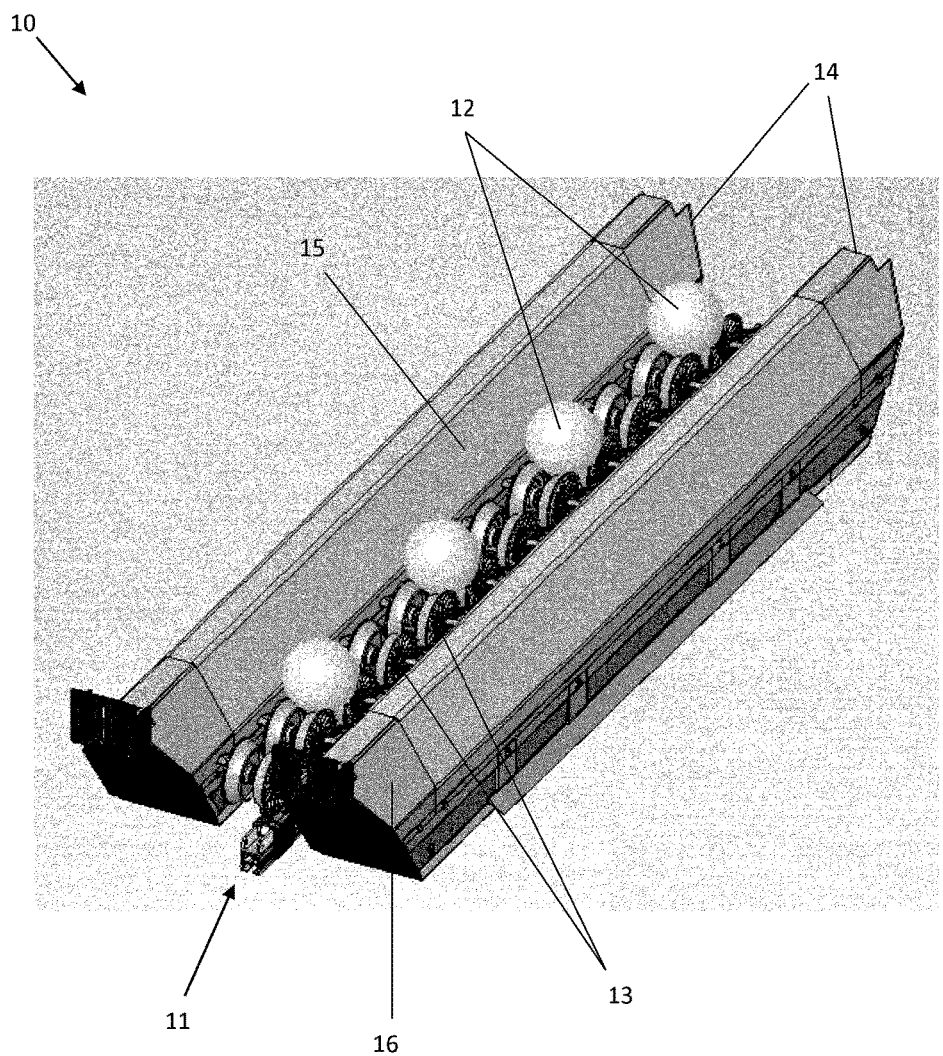
FIG. 1 is an isometric view illustration of part of a conveying system according to one embodiment of the invention.
Figure 2:
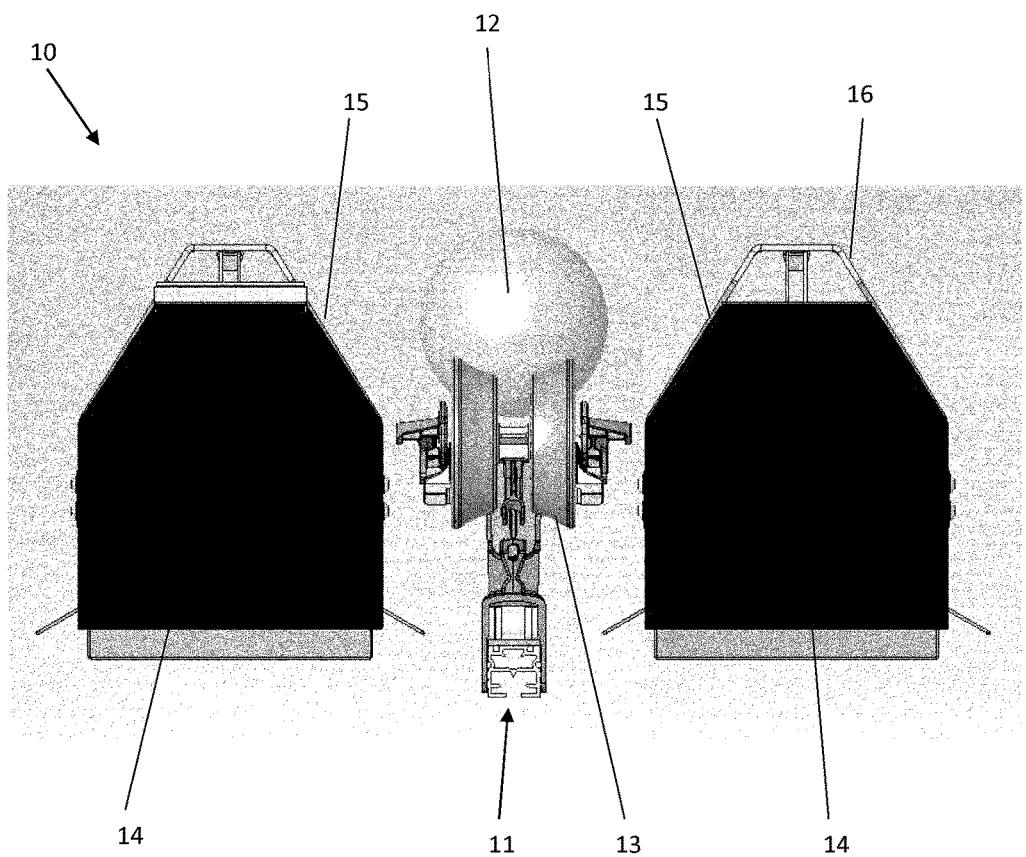
FIG. 2 is an end view illustration of the part of the conveying system shown in FIG. 1.

FIGS. 1 and 2 are isometric and end view illustrations respectively of part of a conveying system 10 according to one embodiment of the invention. Conveying system 10 comprises an endless conveyor 11 which conveys a number of articles 12 along a conveying path. Endless conveyor 11 may be any type of conveyor known in the art. The conveyor 11 illustrated in FIGS. 1 and 2 comprises a plurality of article carriers 13 mounted on an endless belt or chain that is driven by a conveyor drive mechanism. Only a part of the endless conveyor 11 is shown in FIG. 1 and it will be understood that the conveyor continues upstream and downstream on either end of the parts illustrated. The articles 12 are carried by the article carriers in discrete article receiving locations which, in the example of the conveyor 11, are defined between rollers on adjacent article carriers. In other embodiments of the invention, other types and configurations of conveyors may be used.

In FIGS. 1 and 2, articles 12 are shown as round balls for illustration purposes. Conveying system 10 may be used to convey any type of article that is to be inspected and sorted. In one particular example of the invention, conveying system 10 is used to inspect and sort fruit, although other types of article or product may be processed in other embodiments of the invention.

Although only a single conveyor 11 defining a single conveying path is shown in FIGS. 1 and 2, conveying system 10 may convey articles along a plurality of conveying paths. For example, conveying system 10 may comprise a plurality of conveyors each driven by a separate driving mechanism, or the same conveyor may comprise a plurality of rows of article carriers, each defining a conveying path or lane, but driven by the same driving mechanism. For the purposes of this specification, it will be understood that a "conveyor" may refer to a device for driving a plurality of articles in a conveyed direction in one or more paths/lanes, or one or more of the individual paths/lanes along which a number of articles are driven, irrespective of how many separate drive mechanisms are used to convey the articles along those paths/lanes. Typically, the plurality of conveying lanes/paths will be parallel, although in some embodiments, the lanes may not be parallel.

Conveying system 10 may be comprised as part of an article inspection system that inspects articles as they are conveyed by the conveyors 11. Inspection of the articles is performed by image capture means, such as one or more cameras. The conveying system 10 may also be part of an article sorting system. The article sorting system comprises processing means for analysing the images of the inspected articles and generating data as to how the articles should be sorted. The processor controls means for discharging the articles from the conveyors based on the analysis of the images of the articles, for example to multiple destination locations based on size, colour, weight or any other characteristic of the articles, to sort the articles based on the results of the inspection.

Lane Dividing Article Illumination Device

Conveying system 10 further comprises lane dividers 14. Each of lane dividers 14 is an article illumination device positioned adjacent the conveyor 11 (or the conveying path defined by conveyor 11) and is elongate substantially in the same orientation or direction of the conveyor. In FIGS. 1 and 2, only a single conveyor 11 is illustrated. In embodiments that comprise only a single conveyor, lane dividers 14 flank the conveyor 11. However, in embodiments in which the conveying system comprises multiple conveyors 11 all arranged in parallel, lane dividers 14 are positioned between each conveyor 11. It will be understood that the end lane dividers will be adjacent only a single conveyor 11 (the end conveyors). As a result, the lane dividers may alternatively be referred to as lane barriers or edges.

Lane dividers 14 provide a source of diffuse light with which the articles 12 are illuminated. Because of the positioning of the lane dividers 14 substantially at or below the level or height of the articles 12 when conveyed along the conveyor 11, the diffuse light produced by lane dividers 14 illuminates at least side portions of the articles 12. Diffuse light from the lane dividers may also provide some illumination of other parts of the articles 12, for example through reflection off other parts of the conveying system 10. The illumination of the sides of articles 12 by the lane dividers 14, in combination with illumination of the tops of articles by other light sources (as will be described later), provides a more even illumination of articles than prior art systems and therefore improves the accuracy of sorting of conveyed articles.

Figure 3:
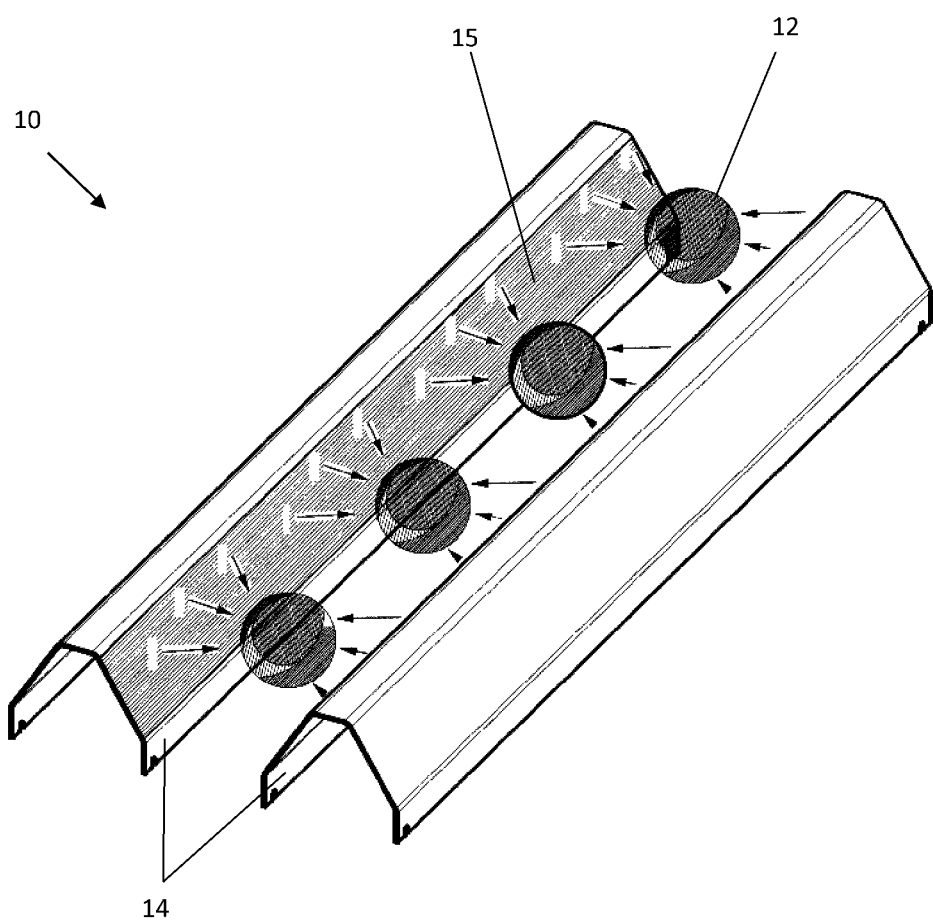
FIG. 3 is a schematic isometric view illustration of the part of the conveying system shown in FIGS. 1 and 2.

In the embodiment of FIGS. 1 and 2, the lane dividers comprise an elongate housing or body 16 and elongate walls 15. The walls 15 face articles 12 when conveyed on the adjacent conveyor 11 to the respective lane divider 14. Lane dividers are configured to act as a source of diffuse light to illuminate the articles and the walls 15 have light emitting surfaces. Walls 15 are formed of, or comprise, a translucent diffuser such that diffuse light produced by one or more light sources housed within the lane dividers is emitted by the walls 15. FIG. 3 is a schematic isometric view illustration of the part of the conveying system 10 shown in FIG. 1. As shown in FIG. 3, diffuse or scattered light from multiple parts of the light emitting surface of walls 15 illuminate articles 12, providing an even illumination of different parts of the articles.

An example of an arrangement of light sources within lane divider 14 is provided below. In other embodiments, light sources are not housed within lane dividers 14 but are configured to project light onto the diffusers in the walls of the lane dividers.

The walls 15 of lane dividers 14 may be angled so that the surface of the walls slants slightly upwards. Where lane dividers 14 have walls with light emitting surfaces on both sides, as in the embodiment of FIGS. 1 and 2 so that walls on either side of each lane divider faces a conveying path, the cross-sectional shape of the lane dividers 14 is in the form of an arch, upturned U or upturned V. The angled aspect to the walls helps to illuminate the lower portion of the sides of articles 12, particularly as the light emitting surfaces of walls 15 are approximately level with the bottom half of articles 12 when conveyed on conveyor 11 in the system of FIGS. 1 and 2. The angle of slant of the walls may differ in other embodiments of the invention and may be chosen to enhance illumination conditions. The angled sides of lane dividers 14 create a valley-like channel through which conveyor 11 moves when passing between the lane dividers, the valley-like channel having a wider gap between the tops of the lane dividers than the lower parts of the lane dividers. The lower edges of the angled walls 15 are positioned close to the article carriers 13 on conveyor 11. If articles 12 become dislodged from the article carriers 13 while being conveyed, then the shape of the angled walls may help to guide the articles back onto the conveyor and to prevent articles falling down between the gap between the conveyor 11 and lane dividers 14. The wider gap between the tops of the walls of adjacent lane dividers also helps let light in from above, promoting a more even illumination of the article 12. The gap also improves the line of sight for cameras that are positioned to inspect the articles 12 when conveyed.

As can be seen in FIG. 1, lane dividers 14 are sufficiently long that the lane dividers, and their light emitting surfaces, flank, or are adjacent to, multiple articles 12 when conveyed on conveyor 11. By way of example only, the light emitting surfaces of walls 15 of lane dividers 14 extend along the length of the conveyor 11 sufficiently far so that around 7 or 8 article receiving locations of the conveyor 11 are immediately adjacent, or perpendicularly opposite, parts of the light emitting surface of the lane dividers 14 (in FIG. 1, articles 12 are illustrated as occupying only every other article receiving location of conveyor 11).

Illumination Cabinet

Figure 4:
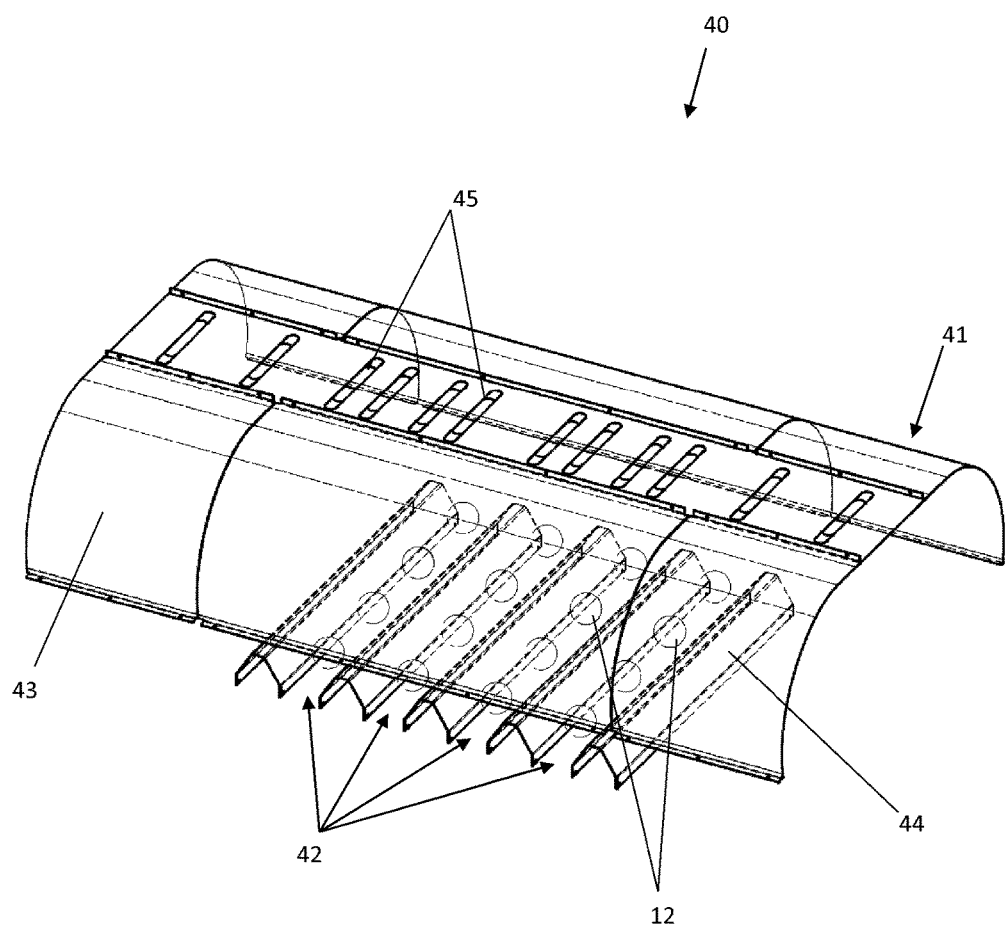
FIG. 4 is an isometric view illustration of part of an article inspection system according to another embodiment of the invention.

FIG. 4 is an isometric view illustration of part of an article inspection system 40 according to an embodiment of the invention. Inspection system 40 comprises multiple conveying systems such as have been described with reference to FIGS. 1-3. Inspection system 40 therefore comprises multiple conveyors (not shown) which convey articles 12 along parallel conveying paths 42 flanked by lane dividers 44. Lane dividers 44 are substantially similar to those described in FIGS. 1-3.

The conveying paths 42 cause articles 12 to pass through an inspection apparatus 41, which may be referred to in the art as a cabinet, and provides an inspection site therein. Inside inspection apparatus 41, the articles are illuminated and imaged so as to be analysed for sorting or other purposes. Cover member 43 covers portions of conveying paths 42 and partly defines the inspection site. Cover member 43 acts to substantially enclose the upper region of the inspection apparatus 41 to reduce the amount of light coming from outside of the inspection apparatus 41 that is incident on the articles 12. In the embodiment shown in FIG. 4, cover member 43 has an arch-like shape with the ends of the arch being positioned above upstream and downstream parts of the conveying paths 42, i.e. with the longitudinal axis of the arch having a direction perpendicular to the conveying direction of the conveyors. The ends of cover member 43 may be open but extend sufficiently far away from the end conveying path 42 that little in the way of light from outside the inspection apparatus 41 can be incident on the articles 12 when conveyed along conveying paths 42. For example, the cover member 43 may extend sufficiently far that there can be no direct illumination of any articles 12 in the inspection site. The extent to which cover member 43 needs to extend transversely away from the end conveying path 42 will depend on a number of factors, including, for example, the height of lane dividers 44, the size of articles 12 and the relative vertical position of the article carriers compared to the vertical position of the lane dividers. Alternatively, the ends of cover member 43 may be closed. The legs or side panels of the arch-shape of cover member 43 extend sufficiently far down above the top of lane dividers 44 to minimise the amount of light entering the inspection site from the upstream and downstream directions relative to the conveyors. Cover member 43 may also extend underneath the conveyors to minimise the amount of light entering the inspection site from underneath. Alternatively, one or more separate covers or light barriers may be provided underneath the conveyors.

Figure 5:
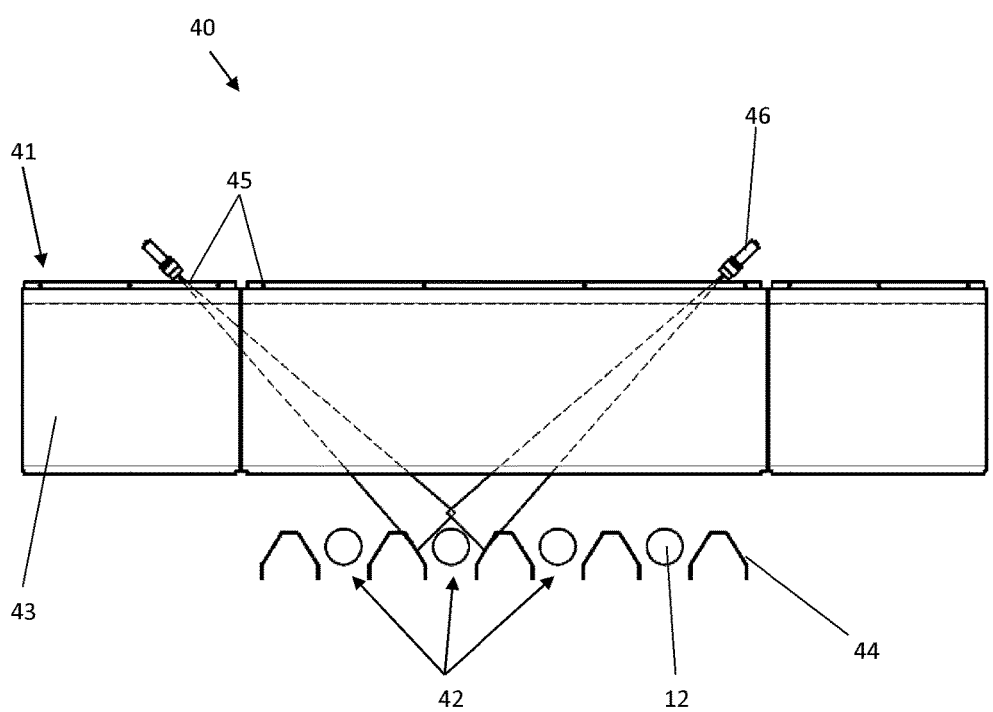
FIG. 5 is an end view illustration of the part of an inspection system shown in FIG. 4.

Cover member 43 may also comprise a number of openings 45, for example in its upper surface. In FIG. 4, openings 45 are slit-like openings disposed in the substantially planar upper region of cover member 43 between the down-turning side panels of the cover member. As shown in FIG. 5, which is an end view illustration of the inspection system 40 shown in FIG. 4, openings 45 allow cameras 46 to capture images of articles 12 when conveyed through the inspection site. Openings 45 may have an opening size substantially similar to a width of the cameras 46 and the cameras 46 may be positioned in opening 45 so as to minimise the amount of light that can enter the inspection site from outside. Openings 45 that are not being used to capture images through may be able to be closed to further minimise the amount of light entering the inside of inspection apparatus 41 from outside.

Lane dividers 44 span across the inspection site substantially between the upstream and downstream ends of the cover member 43. Therefore the inspection site is sufficiently long that multiple articles on each conveyor may be present in the inspection site at any one time.

Inspection apparatus 41 comprises further means for illuminating the articles 12 conveyed along conveying paths 42 with diffuse light in addition to the diffuse light emitted by lane dividers 44 as has been described in relation to FIGS. 1-3. For the purposes of the ensuing description, these further light sources will be referred to as upper light sources because they are configured to illuminate the articles 12 from an aspect substantially above the level of the articles. However, as will be explained, the light sources that provide this further illumination may be positioned in any number of locations and are not necessarily themselves in an upper position.

The upper light sources are not illustrated in FIG. 4 or 5 but, in one embodiment, they are positioned so as to project light upwards onto the bottom surface of cover member 43 but without shining light directly on articles 12. For example, the upper light sources may be mounted proximate the bottom of the ends of cover member 43 behind a barrier to prevent direct illumination of the articles on the conveying paths. Alternatively, they may be provided separate to cover member 43, including below the level or height of articles 12 and project light upwards onto the underside of cover member 43. Cover member 43 preferably has a bottom surface that diffuses light from the upper light sources so that the light from the upper light sources undergoes diffuse reflection before being incident on the articles 12. Additionally, the upper light sources may be covered by translucent diffusers to conduct a first diffusion of light before the light is further diffused by reflection off the bottom surface of cover member 43. Alternatively, the inspection apparatus may comprise upper light sources that directly illuminate the articles with diffuse light, for example through the use of translucent diffusers only. Such lights may be recessed into cover member 43, for example.

Inspection of Articles

In use, articles 12 are conveyed through inspection apparatus 41 by conveyors along the conveying paths 42. One or more cameras 46 image the articles and the captured image data is analysed by an image processor to generate data on the articles 12. The nature of the data that is generated depends on the characteristics of the articles 12 that are inspected, for example how the articles 12 will be sorted. In the case of the inspection of fruit, examples include weight, shape, colour and ripeness. The article characteristic data is used to determine how the articles are to be sorted, for example whether they should be discharged from the conveyors and, if so, to which of a plurality of discharge locations. Based on this determination, discharge means are controlled to discharge articles from the conveyors accordingly.

Figure 6:
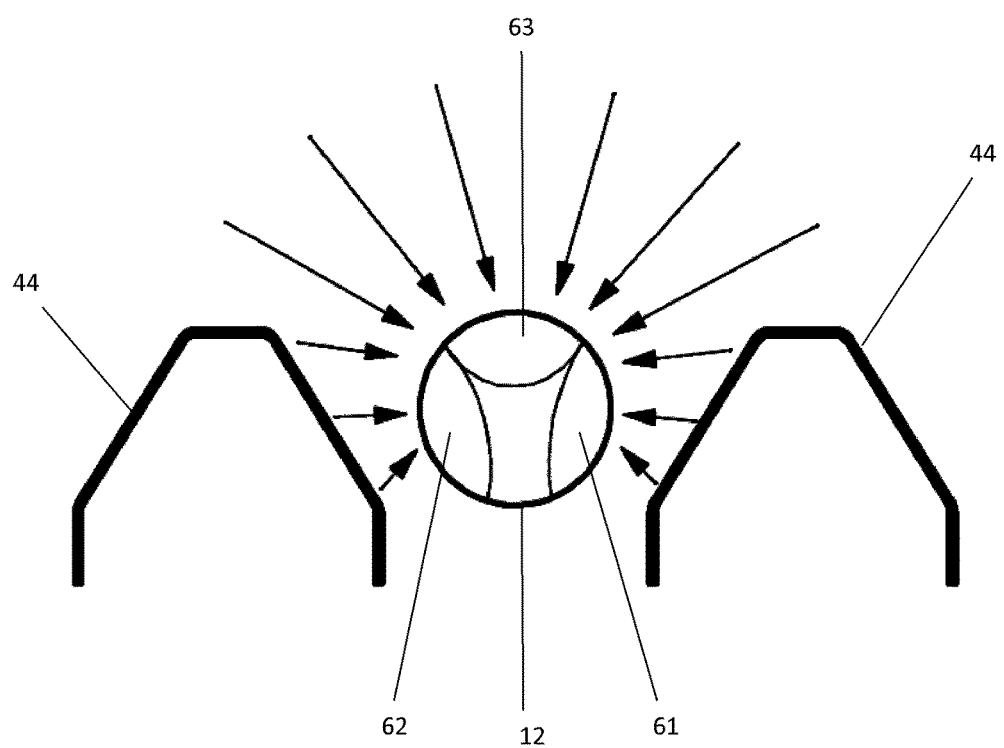
FIG. 6 is a schematic illustration of part of the inspection system shown in FIGS. 4 and 5.

When the images of the articles are captured, the articles are illuminated inside the inspection apparatus 41 by diffuse light from the upper light sources and the light sources inside (or associated with) lane dividers 44. FIG. 6 is a schematic illustration of an article 12 on a conveying path 42 inside inspection apparatus 41 being illuminated by diffuse light from these light sources. The three shaded regions 61, 62 and 63 on article 12 broadly illustrate the parts of the surface of article 12 that are illuminated by the diffuse lane divider light sources (in the case of regions 61 and 62) and the upper light sources (in the case of region 63), although it will be understood that these regions are approximations and typically the regions of illumination from the different light sources will vary continuously across the surface of the article. FIG. 6 illustrates that the distribution of illumination across the surface of article 12 can be made very uniform by the diffuse light sources, which helps reduce image artefacts (e.g. shadows and smears) on the articles and increase the quality of the captured images. In particular, the 'transition' areas of the article's surface, i.e. those that are positioned between or at the intersection of regions 61, 62 and 63 where illumination from one of the light sources is much stronger than the others, may be illuminated to a similar degree of intensity and uniformity to regions 61, 62 and 63, thus ensuring an even blend of illumination from the different light sources.

The intensity or strength of illumination from the respective light sources may be controlled to increase the uniformity of illumination across the surface of the inspected articles. Inspection system 40 may comprise a light intensity controller for controlling the intensity of the upper light sources and/or the lane divider light sources. The controller may be configured to adjust the relative intensities of these light sources so that the intensity of light incident on the articles from all directions is substantially equal. The intensities of the light sources may be set during a calibration process prior to use of the apparatus. The process of calibrating the light sources may involve conveying objects with high reflectivity through the inspection site to help determine the relative intensities from the different light sources. For example, mirror balls may be used.

Conventional diffuse illumination inspection systems are configured so that articles are well illuminated at a specific inspection location in the conveying path but often this means that the quality of illumination deteriorates rapidly as the position of an article is translated away from that specific inspection location along the conveying path. Consequently, inspection of articles in conventional inspection systems is confined to a small inspection location if the quality of inspection is not to be adversely affected. This makes the configuration and control of convention inspection systems difficult and expensive.

Inspection apparatus 41 provides a large region of diffuse illumination along the conveying paths 42. While the illumination conditions may still be greatest in a specific location (for example, for each conveying path, in the middle of the inspection apparatus or at the same distance along the conveying path as the position of camera 46), the illumination conditions do not deteriorate rapidly away from that location. Therefore, imaging articles even when they are translated along the conveying path away from the location of greatest illumination conditions may still result in good image quality, therefore good article inspection and consequently good sorting decisions. This tolerance to article translation results, at least in part, from the elongate nature of the diffuse light emitting surface of the lane dividers 44 along the conveying path.

Inspection apparatus 40 may comprise an image controller that can selectively control illumination of the various light sources for illuminating the inspection site and can also selectively control the capture of images from each camera 46 dependent on the controlled illumination of the different light sources. This enables the lighting conditions to be controlled and improved dependent on the position or other characteristics of the camera that images an article.

Exemplary Lane Divider Illumination Configuration

As has been described, embodiments of the invention provide article illumination devices that border or flank conveying lanes. In relation to the embodiments shown in FIGS. 1-6 the illumination devices are referred to as lane dividers because, with the exception of the end devices, they are positioned between conveying lanes. The lane dividers are configured to emit diffuse light along their length, for example along an elongate light emitting surface.

The lane dividers 14 shown in FIGS. 1 and 2 comprise walls 15 that comprise or are formed in part of a translucent light diffusing material or panel so that light produced or projected inside the lane divider is diffused when being emitted from the lane divider. To increase the degree of diffusion it may be advantageous to incorporate one or more further diffusing members to diffuse the light produced by the lane divider light sources.

Figure 7:
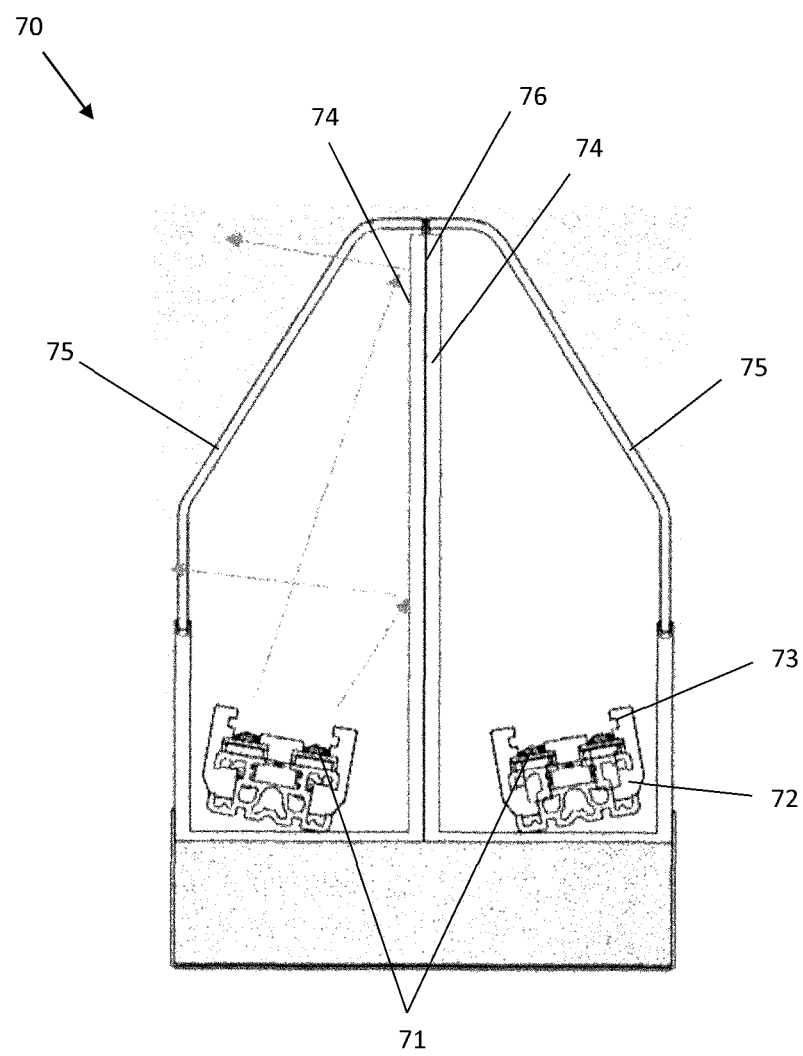
FIG. 7 is a cross-sectional end view illustration of a lane divider according to one embodiment of the invention.

FIG. 7 is a cross-sectional end view illustration of a lane divider 70 according to one embodiment of the invention. Lane divider 70 comprises a plurality of individual sources of non-diffuse light, for example LEDs 71. The LEDs 71 are preferably spaced along the length of the lane divider 70. An equal spacing of LEDs that have the same light intensity will promote a greater uniformity to the intensity of light emitted along the length of lane divider 70. The LEDs 71 are mounted in a rack or mounting 72. The rack 72 includes slots 63 into which may be inserted one or more translucent light diffusers so that all light emitted by the LEDs 71 is diffused by these diffusers. In other embodiments, the translucent light diffusers may be positioned in relation to the LEDs to diffuse the emitted light in any other suitable manner. Also housed within the body of lane divider 70 are one or more reflective light diffusers 74 positioned to further reflect and diffuse light emitted by the LEDs. The reflective light diffusers 74 are positioned so that light can be received from the LEDs and reflected towards the translucent diffusers that form the walls 75 of the lane dividers. In the embodiment shown in FIG. 7 the reflective light diffusers 74 are fixed to an internal wall 76 dividing the interior of lane divider 70 into two halves. Alternatively, the wall 76 may be formed of the reflective light diffusers 74. The components inside lane dividers 70 are configured such that only light that is diffused by first the translucent diffusers covering the LEDs 71, then diffused by the reflective diffusers 74 and finally diffused by the translucent wall diffusers 75 is emitted by the lane dividers (exemplary paths of such light is generally indicated by the arrows in FIG. 7). This arrangement and multiple instances of diffusion help to improve the uniformity of light intensity provided by the lane dividers.

In other embodiments, one or more of the diffusers described in the preceding paragraph may be absent. Furthermore, other embodiments may include other types of light source, for example strip lights oriented along the length of the lane dividers.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention claimed is:

1. An article inspection system comprising:
   one or more endless article conveyors configured to convey articles along one or more conveying paths;
   one or more light sources; and
   one or more lane dividers, each lane divider positioned adjacent one of the one or more conveying paths, each lane divider comprising an elongate housing having a longitudinal axis, the elongated housing having a cross-sectional shape in a plane transverse to the longitudinal axis in a form selected from the group consisting of; an arch, bell-shape, upturned U and upturned V, the housing comprising one or more light diffusers, wherein each light diffuser is positioned substantially at or below the level of the articles when conveyed along the one or more conveying paths so as to illuminate, using light from the one or more light sources, at least side portions of the articles with substantially diffuse light when the articles are conveyed along the one or more conveying path(s);
   each light diffuser comprising an elongate light emitting surface which has a length such that parts of the light emitting surface are substantially adjacent a plurality of articles when the articles are conveyed down the one or more conveying path;
   the article inspection system further comprising at least one camera positioned to image articles conveyed along the one or more conveying paths.

2. An article inspection system as claimed in claim 1, wherein the one or more light diffusers comprise a plurality of first translucent light diffusers and at least a portion of each wall of the one or more lane dividers is formed from one of the first translucent light diffusers.

3. An article inspection system as claimed in claim 2, wherein the one or more light diffusers comprise a plurality of reflective light diffusers and each one or more lane dividers comprises one or more of the reflective light diffusers configured to diffuse and reflect light received from one of the one or more light sources such that the diffuse and reflected light is incident on the respective first translucent light diffuser(s).

4. An article inspection system as claimed in, wherein the one or more light diffusers comprise a plurality of second translucent light diffusers and each one or more lane dividers comprises one or more of the second translucent light diffusers positioned to diffuse light emitted by the one or more light sources so that diffuse light is incident on the reflective one or more light diffuser(s).

5. An article inspection system as claimed in claim 1, wherein each one or more lane dividers further comprises at least one of the one or more light sources for illuminating the articles.

6. An article inspection system as claimed in claim 5, wherein each one or more lane dividers comprises a plurality of the light sources housed by the elongate lane divider housing, the plurality of light sources being spaced along a length of the lane divider.

7. An article inspection system as claimed in claim 1, wherein the inspection system comprises one or more upper light sources configured, in combination with one or more of the light diffusers, to illuminate at least upper portions of the articles with substantially diffuse light when the articles are conveyed along the one or more conveying path(s).

8. An article inspection system as claimed in claim 7, wherein the one or more light sources and the one or more upper light sources are configured to illuminate the articles with substantially equal light intensity.

9. An article inspection system as claimed in claim 7, wherein the inspection system comprises a light intensity controller configured to control intensity of the one or more light sources and the one or more upper light sources.

10. An article inspection system as claimed in claim 7, wherein the inspection system comprises a plurality of cameras and an image controller for selectively controlling each of the plurality of cameras to image the articles conveyed along the one or more conveying paths and for selectively controlling illumination of the one or more light sources and the one or more upper light sources, the selective control of imaging by the plurality of cameras being dependent on selective control of illumination by the one or more light sources and the one or more upper light sources.

11. An article inspection system as claimed in claim 7, wherein the inspection system comprises a cover member configured to substantially cover the one or more conveying paths along at least the part of the length of the one or more conveying paths illuminated by the one or more light sources and to substantially inhibit or prevent light from light sources other than the one or more light sources and the one or more upper light sources from illuminating the articles.

12. An article inspection system as claimed in claim 11, wherein the cover member is comprised of a light diffusing bottom surface configured to diffuse light from the one or more upper light sources so that diffuse light illuminates the upper portions of the articles.

13. An article inspection system as claimed in claim 12, wherein the one or more upper light sources are configured to project light upwards onto the light diffusing bottom surface of the cover member.

14. The inspection sorting system according to claim 1 further comprising:
   discharge means for selectively discharging articles from the article conveyors to one or more discharge locations.

15. The article inspection system as claimed in claim 14, further comprising means for controlling the discharge means based on analysis of images captured by the at least one camera.

16. The article inspection system as claimed in claim 15, further comprising means for generating data indicative of how the articles should be sorted dependent on the analysis of the images.

17. The article inspection system as claimed in claim 15, further comprising analysis means for receiving image data based on the images and analysing the image data to determine characteristics of imaged articles.

* * * * *

UNITED STATES PATENT AND TRADEMARK OFFICE
CERTIFICATE OF CORRECTION

PATENT NO. : 10,099,258 B2  
APPLICATION NO. : 15/564140  
DATED : October 16, 2018  
INVENTOR(S) : Duncan Galbraith, Michael Edmondson and Simon Knightley It is certified that error appears in the above-identified patent and that said Letters Patent is hereby corrected as shown below:

In the Claims

Column 13, Line 60, Claim 4, add the word "claim 3" after the words "as claimed in".

Signed and Sealed this  
Thirty-first Day of December, 2019

Andrei Iancu  
*Director of the United States Patent and Trademark Office*